US00PP09559P

United States Patent [19]

Polys

[11] Patent Number: Plant 9,559

[45] Date of Patent: May 21, 1996

[54] CHRYSANTHEMUM PLANT NAMED 'YELLOW DAVIS'

[75] Inventor: Susan M. Polys, Salinas, Calif.

[73] Assignee: Yoder Brothers, Inc., Barberton, Ohio

[21] Appl. No.: 331,861

[22] Filed: Nov. 1, 1994

[51] Int. Cl.[6] ..... A01H 5/00

[52] U.S. Cl. ..... Plt./82.2

[58] Field of Search ..... Plt./82.2

[56] References Cited

U.S. PATENT DOCUMENTS 4,616,099 10/1986 Sparkes ..... 47/58

OTHER PUBLICATIONS

Broertjes, et al., 1980, "A Mutant of a mutant of a . . . Irradiation of progressive radiation–induced mutants in a mutation breeding programme with *Chrysanthemum morifolium*", Euphytica, 29:525–530.

Gosling, ed., 1979, "The Chrysanthemum Manual—6th edition", The National Chrysanthemum Society, London, Essex Telegraph Press, Ltd., pp. 329–336.

Broertjes, et al., 1978, "Application of Mutation Breeding Methods In the Improvement of Vegetatively Propagated Crops", Elsevier Sci. Pub. Co., New York, pp. 162–175.

Searle,et al., 1968, "Chrysanthemums the Year Round", Blanford Press, London, pp. 27–29, 320–327.

Chan, 1966, "Chrysanthemum and rose mutations induced by X–rays", Am. Soc. Hort. Sci. Proc., pp. 613–620.

Broertjes, 1966, "Mutation breeding of Chrysanthemums", Euyphytica, 15:156–162.

Dowrick, et al., 1966, "The induction of mutations in Chrysanthemum using X– and gamma radiation", Euphytica, 15:204–210.

*Primary Examiner*—Howard J. Locker
*Attorney, Agent, or Firm*—Foley & Lardner

[57] ABSTRACT

A Chrysanthemum plant named Yellow Davis particularly characterized by its flat capitulum form; daisy capitulum type; yellow ray floret color; diameter across face of capitulum of 64 to 70 mm when fully opened, when grown as a pinched spray pot mum; photoperiodic flowering response to short days of 56 to 61 days; plant height, with 15 to 16 long days after sticking unrooted cuttings and with 1 to 2 applications of 2500 ppm B-9 SP, ranges from 20 to 28 cm when grown as a pinched pot mum with 4 cuttings in a 15 cm pot; branching pattern is spreading, each plant having 4 to 6 laterals after pinch; and recommended as spray pot mum.

1 Drawing Sheet

The present invention comprises a new and distinct cultivar of Chrysanthemum, botanically known as *Dendranthema grandiflora,* and referred to by the cultivar name Yellow Davis.

Yellow Davis, identified as 5439 (84-382J03), is a product of a mutation induction program. The new cultivar was discovered and selected by Susan M. Polys on Apr. 13, 1992 in a controlled environment in Salinas, Calif., as one flowering plant within a flowering block established as rooted cuttings from stock plants which had been exposed as unrooted cuttings to an X-ray source of 1500 rads in Fort Myers, Fla., on Nov. 21, 1991. The irradiated parent cultivar was the cultivar identified as Light Davis, disclosed in U.S. Plant Pat. No. 8,293.

The irradiation program resulting in Yellow Davis had as its primary objective the expansion of color ranges of the parent cultivar Light Davis. The irradiation program comprised irradiating cuttings of the parent cultivar at irradiation levels of 1500 and 1750 rads. A total of 541 cuttings harvested from a total of 150 irradiated plants were planted on Feb. 24 and Feb. 10, 1992. Of these, 4 initial selections were made, which selections were then revegetated and reflowered. Three consecutive flowerings resulted in discarding 3 of the original 4 selections on Dec. 21, 1992. Continued flowering trials resulted in the decision to introduce the one remaining selection as Yellow Davis.

The first act of asexual reproduction of Yellow Davis was accomplished when vegetative cuttings were taken from the initial selection in June 1992 in a controlled environment in Salinas, Calif., by technicians working under supervision of Susan M. Polys.

Horticultural examination of controlled flowerings of successive plantings has shown that the unique combination of characteristics as herein disclosed for Yellow Davis are firmly fixed and are retained through successive generations of asexual reproduction.

Yellow Davis has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Yellow Davis, which, in combination, distinguish this Chrysanthemum as a new and distinct cultivar.

1. Flat capitulum form.
2. Daisy capitulum type.
3. Yellow ray floret color.
4. Diameter across face of capitulum of 64 to 70 mm when fully opened, when grown as a pinched spray pot mum.
5. Photoperiodic flowering response to short days of 56 to 61 days.
6. Plant height, with 15 to 16 long days after sticking unrooted cuttings and with 1 to 2 applications of 2500 ppm B-9 SP, ranges from 20 to 28 cm when grown as a pinched pot mum with 4 cuttings in a 15 cm pot.
7. Branching pattern is spreading, each plant having 4 to 6 laterals after pinch.
8. Recommended as spray pot mum.

The accompanying photographic drawing is a side view of a potted mum of Yellow Davis, with 4 cuttings in a 15 cm pot, with the colors being as nearly true as possible with illustrations of this type.

Of the commercial cultivars known to the inventor, the most similar in comparison to Yellow Davis is the parent cultivar Light Davis. All traits of Yellow Davis are similar to those of Light Davis except for ray floret color. The ray floret color of Yellow Davis is yellow, compared with the light red-purple ray floret color of Light Davis.

In the following description color references are made to The Royal Horticultural Society Colour Chart. The color values were determined on plant material grown as a pinched spray pot mum in Salinas, Calif. on Jun. 22, 1993.

Classification:

*Botanical.*—*Dendranthema grandiflora* cv Yellow Davis.

*Commercial.*—Flat daisy spray pot mum.

INFLORESCENCE

A. Capitulum:

*Form.*—Flat.

*Type.*—Daisy.

*Diameter across face.*—64 to 70 mm when fully opened.

B. Corolla of ray florets:

*Color (general tonality from a distance of three meters).*—Yellow.

*Color (upper surface).*—7A to 7B.

*Color (under surface).*—7B to 7C.

*Shape.*—Straight, oblong, slightly ribbed.

C. Corolla of disc florets:

*Color (mature).*—9A.

*Color (immature).*—144B.

D. Reproductive organs:

*Androecium.*—Present on disc florets only; scant to no pollen.

*Gynoecium.*—Present on both ray and disc florets.

PLANT

A. General appearnce:

*Height.*—20 to 28 cm when grown as a pinched pot mum with 15 to 16 long days prior to start of short days, with 1 to 2 applications of 2500 ppm B-9 SP.

*Branching pattern.*—Spreading, with 4 to 6 laterals after pinch.

B. Foliage:

*Color (upper surface).*—147A.

*Color (under surface).*—147B.

*Shape.*—Deeply lobed and serrated.

I claim:

1. The new and distinct Chrysanthemum plant named Yellow Davis, as described and illustrated.

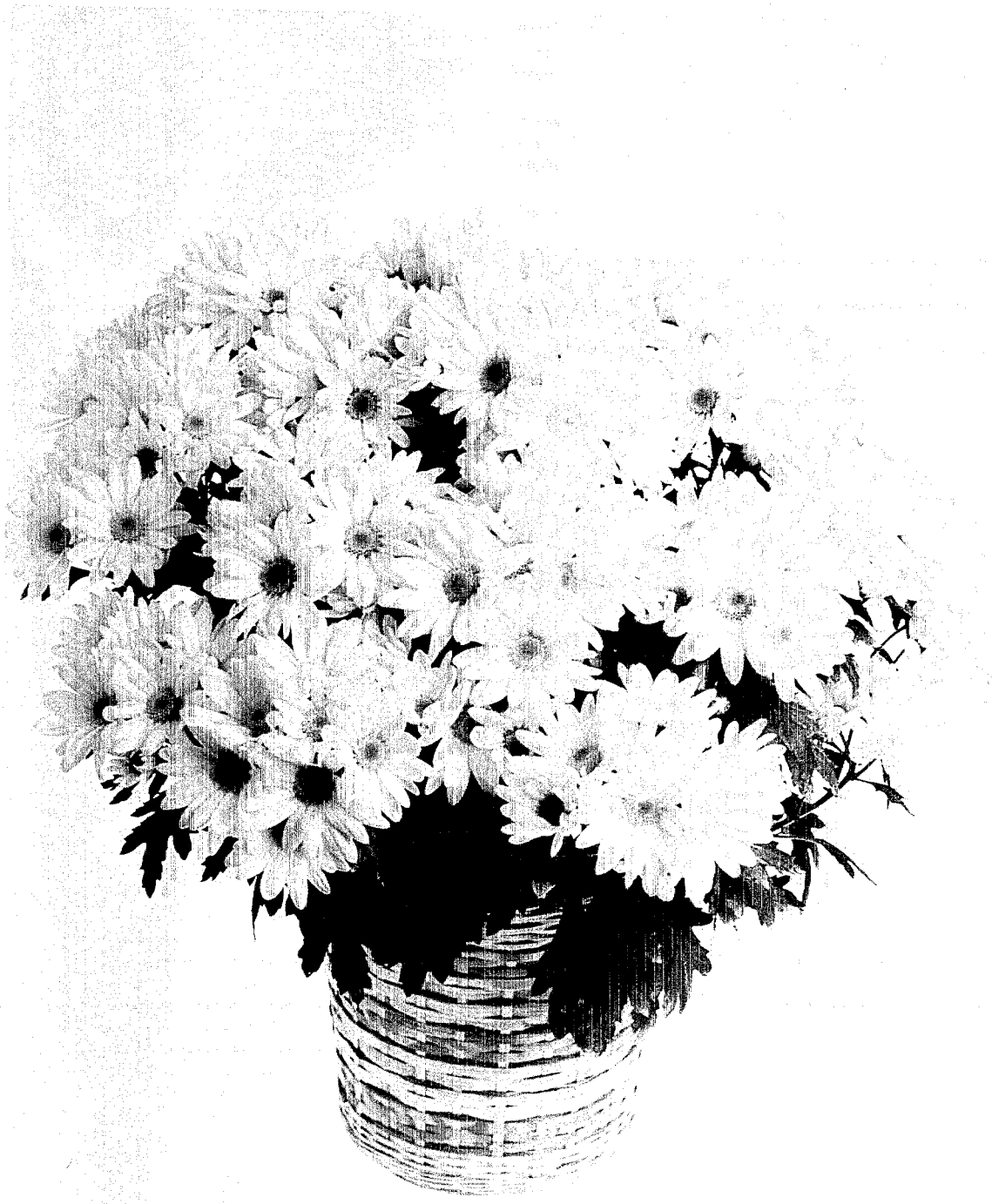

* * * * *